United States Patent
Ross

(10) Patent No.: US 7,901,380 B2
(45) Date of Patent: Mar. 8, 2011

(54) IRIS SEAL FOR SURGICAL PORT

(75) Inventor: Adam J. Ross, Prospect, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/467,363

(22) Filed: May 18, 2009

(65) Prior Publication Data

US 2009/0326463 A1 Dec. 31, 2009

Related U.S. Application Data

(60) Provisional application No. 61/075,515, filed on Jun. 25, 2008.

(51) Int. Cl.
*A61M 5/178* (2006.01)
(52) U.S. Cl. .............. 604/167.06; 604/167.01
(58) Field of Classification Search ............ 604/167.01, 604/167.06, 256, 264, 165.04
See application file for complete search history.

(56) References Cited

U.S. PATENT DOCUMENTS

| | | | |
|---|---|---|---|
| 3,785,265 A | 1/1974 | Lardean | |
| 4,598,741 A * | 7/1986 | Johnson et al. | 141/5 |
| 5,382,230 A | 1/1995 | Bonn | |
| 5,480,410 A | 1/1996 | Cuschieri et al. | |
| 5,603,702 A | 2/1997 | Smith et al. | |
| 7,628,787 B2 * | 12/2009 | Sartor et al. | 606/41 |
| 2008/0284114 A1 * | 11/2008 | Price et al. | 277/626 |

FOREIGN PATENT DOCUMENTS

| | | |
|---|---|---|
| EP | 0550069 | 7/1993 |
| EP | 1994896 | 11/2008 |
| WO | WO2004/110286 | 12/2004 |

OTHER PUBLICATIONS

European Search Report for corresponding EP 09251602 date of mailing is Sep. 16, 2009 (3 pages).

* cited by examiner

*Primary Examiner*—Nicholas D Lucchesi
*Assistant Examiner*—Brooke M Matney

(57) ABSTRACT

The present disclosure is directed to a surgical portal apparatus for use during a minimally invasive procedure. In one aspect, the apparatus includes a housing and a portal member extending distally from the housing, defining a longitudinal axis. The apparatus also has an iris seal including a plurality of leaf members, disposed within the housing. The leaf members are adapted for pivoting relative to the housing, to control the dimensioning of a passage in response to the insertion of a surgical object. The leaf members are not directly linked to each other to provide for off-axis movement of the surgical object. The apparatus further includes an actuation mechanism, including a motor and a sensor, operatively connected to the leaf members and adopted for movement upon the introduction of the surgical object.

22 Claims, 5 Drawing Sheets

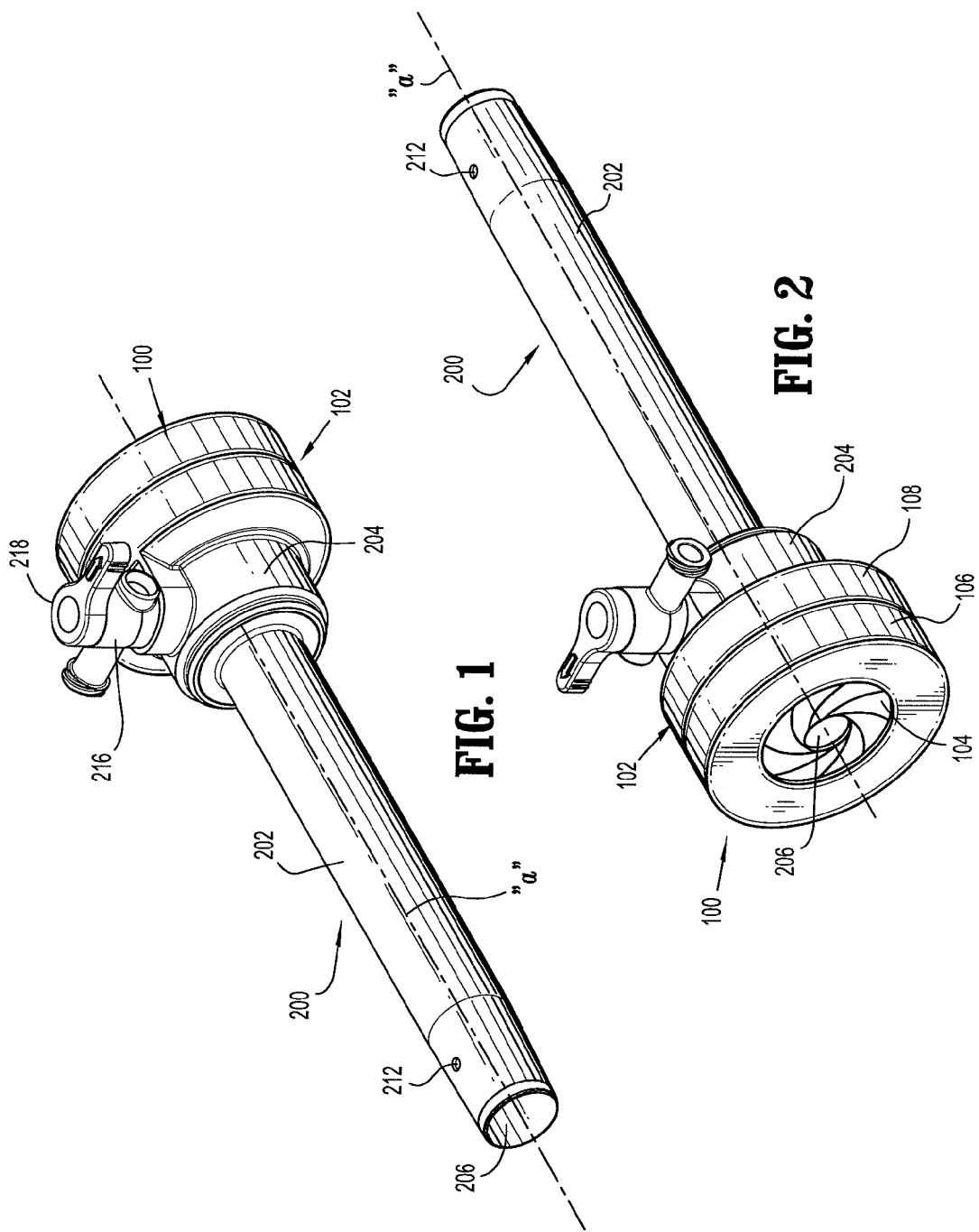

IRIS SEAL FOR SURGICAL PORT

CROSS REFERENCE TO RELATED APPLICATION

The present application claims the benefit of and priority to U.S. Provisional Application Ser. No. 61/075,515, filed on Jun. 25, 2008, the entire contents of which are incorporated herein by reference.

BACKGROUND

1. Technical Field

The present disclosure relates to a device, and a method of use thereof, for facilitating access to a patient's internal cavities during a surgical procedure. More particularly, the present disclosure relates to a surgical apparatus adapted for insertion into an incision in tissue, and for the sealed reception of one or more surgical objects, so as to form a substantially fluid-tight seal with both the tissue and the surgical object, or objects.

2. Background of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure provides a surgical portal apparatus with a seal assembly, which will allow a surgeon to efficaciously utilize instruments of varying diameter in a surgical procedure. This seal assembly obviates the need for multiple adapters to accommodate instruments of varying diameter by providing a seal with an adjustable opening. One embodiment is directed to a surgical portal apparatus having an iris seal for use with a surgical access device. In accordance with one aspect of the present disclosure, the surgical portal apparatus includes a housing, a portal member extending from the housing, and an iris seal disposed within the housing to limit the flow of gas through the portal apparatus. The portal member is dimensioned for positioning within tissue. The portal apparatus includes a longitudinal opening to permit passage of a surgical object through the portal apparatus. The iris seal defines a central opening and contains a plurality of leaf members adapted for movement to control the diameter of the opening.

Pivotal mounting of the leaf members relative to the housing allow the leaf members to move from a first relative position, having an initial diameter passage, to a second relative position, having a different diameter passage. The leaf members are movable, in response to an introduction of a surgical object, to establish a substantial sealing relationship with the surgical object. Movement is accomplished by an actuation mechanism acting upon the leaf members. The actuation mechanism includes a motor with resistive circuitry. The resistive circuitry is configured to detect the load on the motor and stops the motor when a specific load is detected. The motor releasably holds the load torque on the leaf members, in the second relative position, causing a constant seal with the surgical object.

The surgical portal apparatus includes a switch positioned within the housing. The engagement of the switch activates the motor, and thereby causing movement of the leaf members of the iris seal. As a result, the leaf members move from the first relative position to the second relative position. The switch may be located proximal to the iris seal and have a delay mechanism to provide a preset amount of time before actuating the iris seal. The delay allows the surgical object to enter the surgical portal apparatus before the iris seal closes upon the surgical object.

In another embodiment, the switch is located distal to the iris seal and adapted to be engaged by the surgical object during introduction of the surgical object within the housing. In still another embodiment, the surgical portal apparatus includes a manual switch, mounted to the housing and operatively connected to the leaf members of the iris seal. A clinician engages the manual switch to move the leaf members between the first and second relative positions.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

FIG. 1 is a right, perspective view of a trocar assembly and a seal assembly in accordance with the principles of the present disclosure;

FIG. 2 is a left, perspective view of a trocar assembly and a seal assembly in accordance with the principles of the present disclosure;

Figure 3:
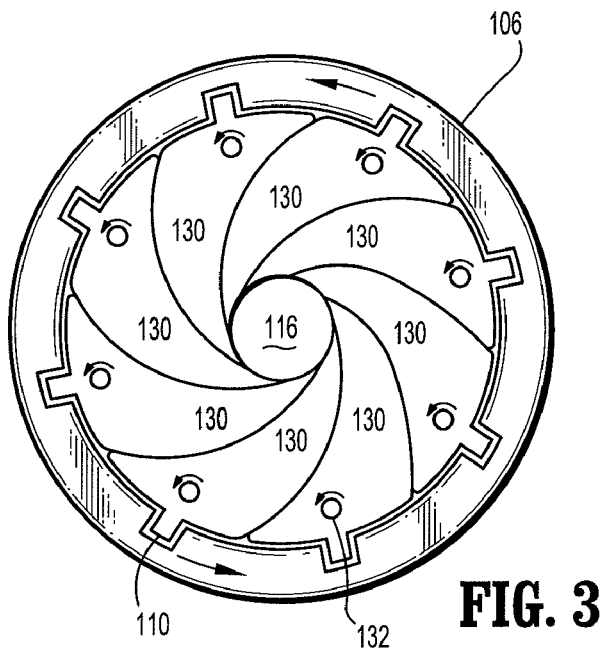
FIG. 3 is a top view of the trocar and seal assemblies in accordance with the embodiment of FIGS. 1-2.

Other features and advantages of the present disclosure will become apparent from the following detailed description, taken in conjunction with the accompanying drawings, which illustrate, by way of example, the principals of the invention.

DETAILED DESCRIPTION

The seal assembly of the present disclosure provides a substantial seal between a body cavity of a patient and the outside atmosphere, before and after insertion of an instrument through the trocar assembly. Moreover, the seal assembly of the present invention is capable of forming a gas tight seal with instruments of varying diameters, e.g., from 5 mm to 15 mm. The flexibility of the present seal assembly greatly facilitates endoscopic surgery, where a variety of instruments having differing diameters is often needed during a single surgical procedure.

The seal assembly maintains a fluid tight interface during the introduction and manipulation of various types of instrumentation to preserve the atmospheric integrity of a surgical procedure from gas and/or fluid leakage. Specifically, the seal assembly greatly reduces the force required for introduction and removal of the instrumentation. The fluid tight interface minimizes the entry and exit of gases and/or fluids to/from the body cavity. Examples of instrumentation adopted for insertion through a trocar and/or trocar assembly include clip appliers, graspers, dissectors, retractors, staplers, laser probes, photographic devices, endoscopes and laparoscopes, tubes, and the like. Such instruments will be collectively referred to as "surgical objects".

By virtue of its features, the seal assembly starts by defining a large diameter or interval dimension and then closes to a smaller diameter. The seal is fully open in the "at rest" position and is capable of fully closing to prevent the escape of fluid when activated. The seal assembly may close around the surgical object. The ability to close around the surgical object minimizes insertion forces and decreases the probability of compromising the seal. A duck-bill seal or zero seal may be used in conjunction to aid in preventing the escape of fluid during insertion and extraction of a surgical object.

In the following description, as is traditional, the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-2 illustrate the seal assembly 100 of the present disclosure mounted to a trocar assembly 200. Trocar assembly 200 may be any conventional trocar suitable for the intended purpose of accessing a body cavity and permit the introduction of instruments therethrough. Trocar assembly 200 is particularly adapted for use in laparoscopic surgery, where the peritoneal cavity is insufflated with a suitable gas, e.g., $CO_2$, to raise the cavity wall from the internal organs therein. Trocar assembly 200 is typically used with an obturator assembly (not shown). The obturator assembly, a sharp pointed instrument positionable within the passageway of the trocar assembly 200, is utilized to penetrate the abdominal wall. Then the obturator is subsequently removed from the trocar assembly 200 to permit introduction of the surgical instrumentation used in the procedure.

With reference to FIGS. 1-2, trocar assembly 200 includes a trocar housing 204 mounted to an end of the sleeve 202. Any means for mounting trocar sleeve 202 to trocar housing 204 are envisioned, including threaded arrangements, bayonet coupling, snap-fit arrangements, adhesives, etc. Additionally, trocar sleeve 202 and trocar housing 204 may be integrally formed.

Trocar sleeve 202 defines a longitudinal axis "a" extending along the length of sleeve 202. Further, sleeve 202 defines an internal longitudinal passage 206 dimensioned to permit passage of surgical objects. Adjacent the distal end of trocar sleeve 202 is aperture 212, which extends through the wall of sleeve 202. Aperture 212 permits passage of insufflation gases through trocar sleeve 202 during the surgical procedure.

The diameter of sleeve 202 may vary, but, typically ranges from about 10 mm to about 15 mm for use with the seal assembly 100 of the present disclosure. Trocar housing 204 includes port opening 214 and luer fitting 216 positioned within the port opening 214. Luer fitting 216 is adapted for connection to a supply for insufflation, and incorporates valve 218 to selectively open and close the passage of the luer fitting 216. Sleeve 202 may be formed of stainless steel or other rigid materials such as a polymeric material or the like. Sleeve 202 may be clear or opaque.

With continued reference to FIGS. 1-4, seal assembly 100 will be discussed in detail. Seal assembly 100 may be a separate component from trocar assembly 200 and, accordingly, adapted for releasable connection to the trocar assembly 200. Alternatively, seal assembly 100 may be incorporated as part of trocar assembly 200 forming a single unit. Seal assembly 100 includes a seal housing, generally identified as reference numeral 102, and iris seal 104, which is disposed within the seal housing 102.

Seal housing 102 contain the sealing components of the assembly, and defines the outer valve or seal body of the seal assembly 100. Seal housing 102 also defines central seal housing axis "b" which is preferably parallel to and coincident with the axis "a" of trocar sleeve 202. Seal housing 102 is formed from the assembly of two housing components, namely, first housing component 106 and second housing component 108. Housing components 106 and 108 may be assembled by any of the aforementioned connection means discussed with respect to trocar housing 204.

Figure 4:
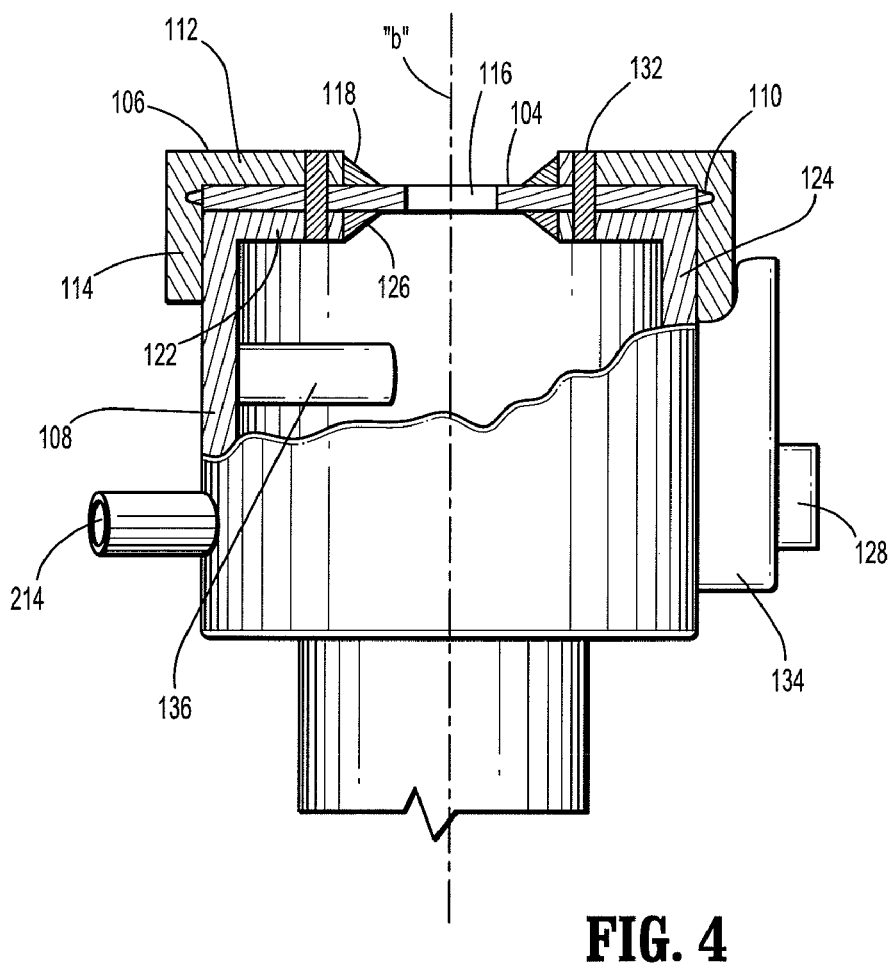
FIG. 4 is a side cross-sectional view of the trocar and seal assemblies in accordance with the embodiment of the present disclosure.

First housing component 106 defines inner or proximal guide wall 112 and outer cylindrical wall 114, which is disposed radially outward of the proximal guide wall 112. Outer cylindrical wall 114 surrounds proximal guide wall 112 and extends distally. Proximal guide wall 112 defines central passage 116 and laterally confines the instrument within the seal housing 102. As best shown in FIG. 4, proximal guide wall 112 defines a maximum diameter opening capable of receiving a surgical object. Proximal guide wall 112 further includes a circular seal 118.

Second housing component 108 includes transverse wall 122 and cylindrical portion 124. Transverse wall 122 includes an inner circular seal 126 about central passage 116. Cylindrical portion 124 is dimensioned to mate with outer wall 114 of first housing component 106. It is envisioned that outer wall 114 defines a scalloped outer surface 114a, which provides for gripping engagement by the user.

Figure 5:
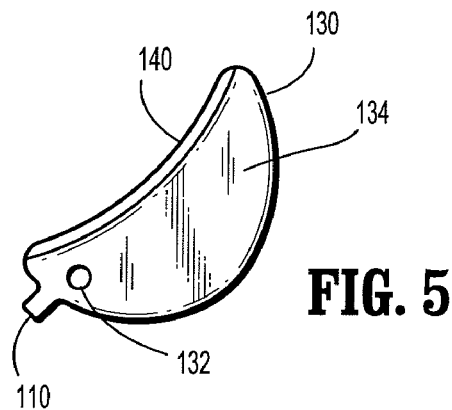
FIG. 5 is a top view of a leaf member in accordance with the present disclosure.

Referring now to FIGS. 3-5, iris seal 104 is mounted between the first housing component 106 and second housing component 108. Iris seal 104 comprises a plurality of leaf members 130. Each leaf member 130 overlaps an adjacent leaf member 130. As shown in FIG. 5, leaf member 130 has a leaf body 134, a leading edge 140, a pin 110, and a hole in the leaf body 132.

Leaf members 130 may be fabricated from a single suitable elastomeric material and have sufficient resiliency to form a seal about an inserted objected. Suitable materials include, but are not limited to polyurethane and copolyester. To minimize friction, the elastomeric materials may be coated with silicon, the product polytetrafluoroethylene sold under the trademark TEFLON, or the like. The leading edge 140 may be fabricated from a different material than the leaf body 134.

Figure 6:
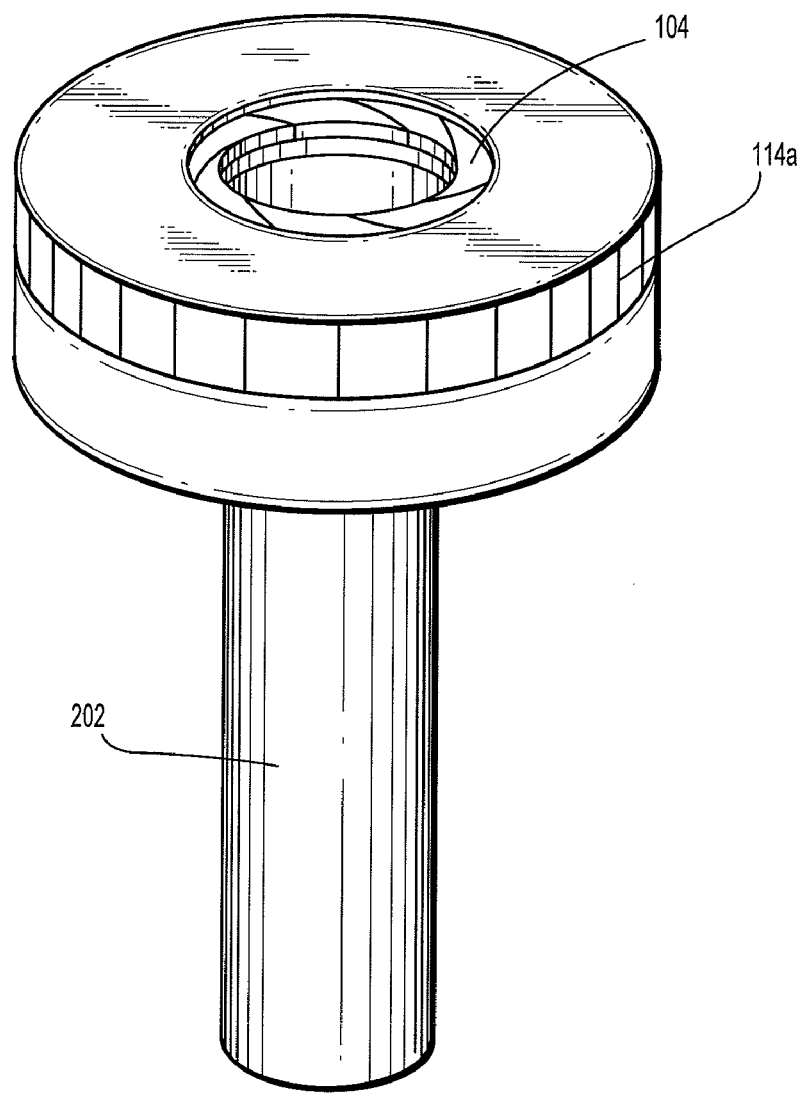
FIG. 6 is a rear, perspective view of a trocar assembly and a seal assembly in accordance with the embodiment of the present disclosure.
Figure 7:
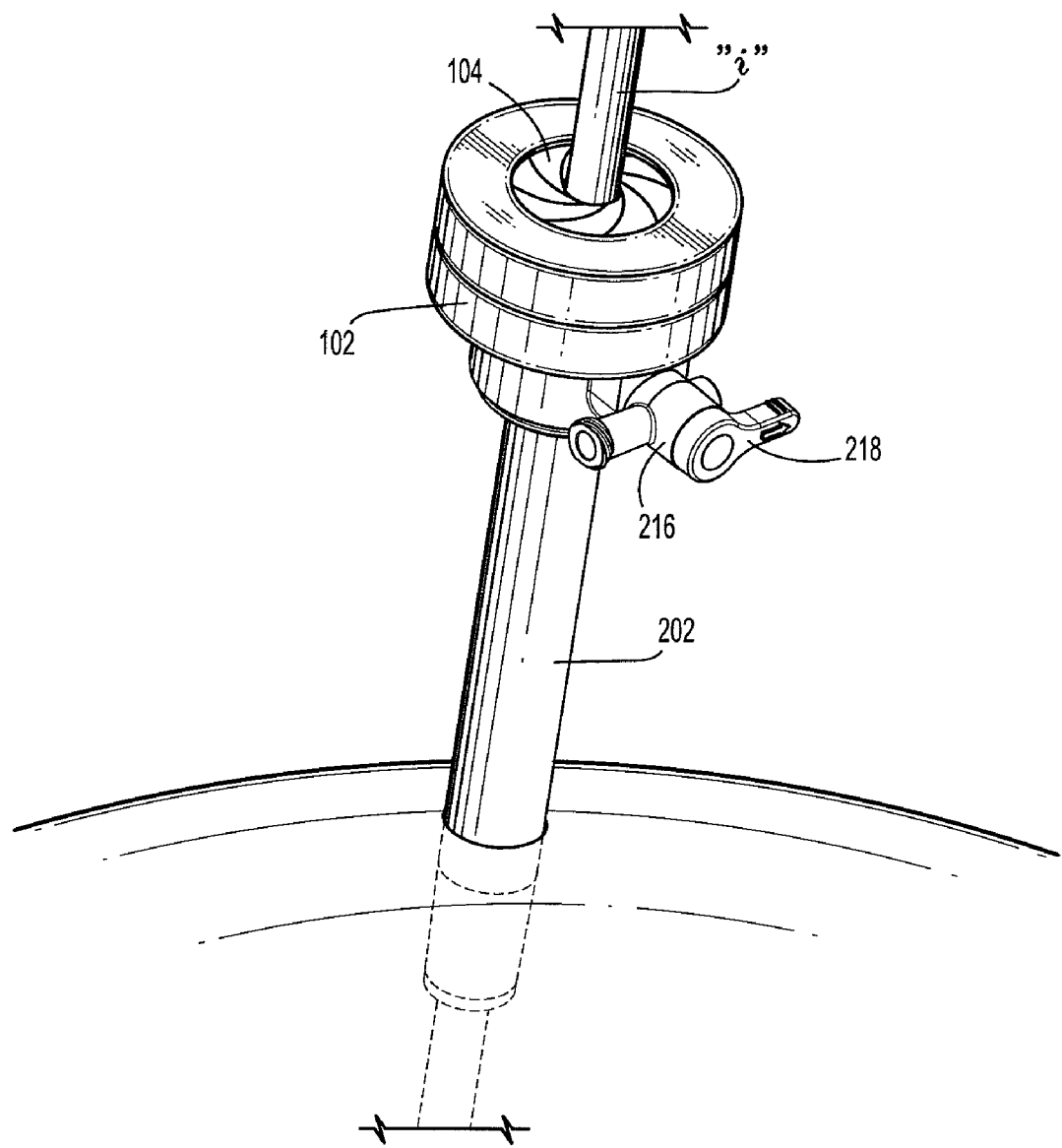
FIG. 7 is a view illustrating the trocar assembly and seal assembly accessing an internal cavity with an instrument introduced therein in accordance with the present disclosure.
Figure 8:
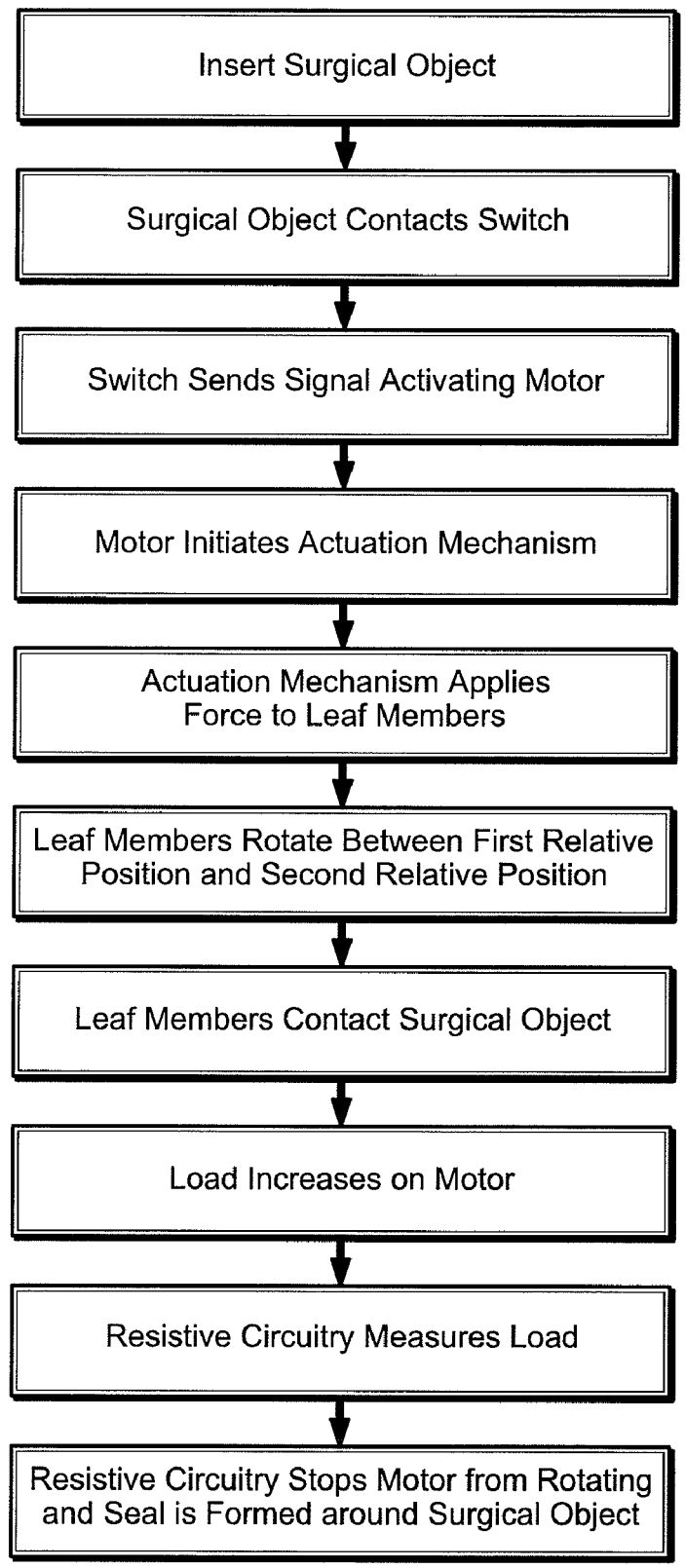
FIG. 8 is a flow chart illustrating one method of operation of the trocar assembly in accordance with the present disclosure.

Iris seal 104 is completely open when the seal assembly 110 is not activated. Leaf members 130 rotate from a first relative position, substantially open, to a second relative position, substantially closed. Leaf members 130 can also rotate to a second relative position forming a seal around the surgical object "i" as shown in FIG. 6. The amount a leaf member 130 rotates will determine the dimension of the central passage 116.

The assembled components are held together by a series of screws 131, or other positive fastening means, through circumferentially spaced holes 132. Holes 132 extend through the iris seal 104 and the second housing component 108. The single attachment point, of each leaf member 130, allows pivoting about the respective fastener 131. This pivoting allows leaf members 130 to change between first and second relative positions. A pin 110, located radially outward from the hole 132, attaches to an actuation mechanism to provide a force upon the leaf members 130. The force acts in a direction out of alignment with the pivot point, causing a moment. This moment forces the leaf members 130 to rotate.

It is appreciated that the pin can be located elsewhere on the leaf member 130. Further, it is appreciated that a moment applied thru hole 132 will cause the leaf members 130 to rotate about a pin 110, and that rotation and applied force can act through two pins or two holes. Further still, the leaf members 130 may slide radially instead of rotate.

The actuation mechanism moves leaf members 130 between the first relative, or open position, and the second relative position to engage the surgical object and establish a sealing relation therewith, or to close the iris seal. The actuation mechanism includes a motor 134 and an associated switch 136. The motor 134 may be any suitable miniature electric motor that is battery powered. The motor output is operatively connected to the leaf members 130 of iris seal 104 in a manner to effect pivotal movement of the leaf members 130 between the first and second relative positions. Various means of connecting the leaf members 130 and the motor 134 are envisioned and appreciated by one skilled in the art.

The motor is activated by switch 136. As the inserted instrument contacts switch 136, the triggered switch activates the motor 134. The motor 134 then applies a force via the actuation mechanism to the leaf members 130. As illustrated in FIGS. 3 and 4, the first housing member 106 is part of the actuation mechanism in this embodiment. The motor 134 acts upon the first housing member 106 to cause the housing member to rotate. Recesses in the outer wall 114 match and accept pins 110 of the leaf members 130. As the first housing member 106 rotates, the force from the motor 134 is translated to the leaf member pins 110. As a result, the motor 134 causes the leaf members 130 to rotate between relative positions. The iris seal closes when wall 114 rotates counterclockwise and the seal opens when the wall 114 rotates clockwise.

The motor 134 draws an electrical current to operate. This current can be measured by a resistive circuitry 128 associated with the motor 134. Alternative uses of resistive circuitry to measure the load upon the motor 134 are envisioned. Once a predetermined load is detected, by the resistive circuitry 128, the motor 134 stops in place and releasably holds the leaf members 130 in the second relative position.

Although a motor is disclosed as part of the actuation mechanism, it is appreciated that the actuation mechanism can be manually operated by a clinician. A clinician can activate the iris seal 104 in several ways. One way to activate the iris seal 104 is by manually rotating the scalloped outer surface 114a. A manual lever may also be connected to a mechanism that rotates the leaf members 130.

Switch 136 is located within the housing 102, between the iris seal and the distal end. As the surgical object "i" is introduced into the center passage 116, the switch 136, which is operatively connected to the motor, is engaged and activates the motor 134. The iris seal 104 then constricts around the surgical object. Thus, the leaf members 130 move from a first relative position to a second relative position around the surgical object. It is also anticipated that the switch is a sensor, capable of determining the size and location of the surgical object. The sensor may interact with a central process unit to determine the individual leaf members 130 to actuate and the degree of actuation. When the surgical object disengages the switch 136, the iris seal 104 opens and allows the surgical object to be removed without damaging the iris seal. Once the switch is deactivated, the force required to remove the surgical object decreases.

It is appreciated that the switch 136 is located proximal to the iris seal 104 and includes a delay mechanism. The delay mechanism may be designed as part of the switch 136, the motor 134, or as a separate part of the electrical system. The delay mechanism provides a preset amount of time before actuating the iris seal. This preset amount of time allows the surgical object to be placed in the central passage 116 and positioned before iris seal 104 closes. In another alternative, the switch is manually operated by a clinician once the surgical object is in place.

Another envisioned configuration has the leaf members 130 interconnected, so that a force on one causes all leaf members 130 to pivot. This interconnectivity prevents the leaf members 130 from rotating independently, to form an off center seal. Thus, the center of the opening is fixed. One alternative for providing off center positioning of the surgical object is to connect, independently, each leaf member pin via spring to the actuating force. The spring allows some leaf members 130 to be biased, while allowing the other leaf members 130 to rotate a greater degree. It is appreciated that the spring force is adjusted/adjustable so that the leaf members 130 rotate enough to stop gaseous flow around the surgical object, while the clinician manipulates the surgical object within the iris seal.

It is further envisioned that the leaf members may be attached and activated through a series of springs and levers to allow the entire seal assembly to float within the housing assembly. A floating seal assembly could be interconnected and still provide off center movement of a surgical instrument.

What is claimed:

1. A surgical portal apparatus comprising:
a housing;
a portal member extending from the housing, the portal member dimensioned for positioning within tissue, the portal member defining a longitudinal axis and having a longitudinal opening for permitting passage of a surgical object;
an iris seal disposed within the housing and defining an opening therethrough and being adapted to establish a substantial sealing relationship with the surgical object introduced within the opening, the iris seal including a plurality of leaf members adapted for movement relative to the longitudinal axis between a first relative position where the leaf members permit passage of the surgical object and a second relative position where the leaf members establish a substantial seal about the surgical object; and an actuation mechanism operatively coupled with the leaf members to move the leaf members between the first relative position and the second relative position, the actuation mechanism including a motor and resistive circuitry, the resistive circuitry adapted to detect an increase of load on the motor thereby causing the actuation mechanism to releasably secure the leaf members in the second relative position.

2. A surgical portal apparatus as defined in claim 1, wherein the leaf members of the iris seal are pivotally mounted relative to the housing, and adapted for pivotal movement between a first relative position and a second relative position.

3. A surgical portal apparatus as defined in claim 1, wherein the actuation mechanism is actuable in response to introduction of the surgical object to cause the leaf members to move between the first relative position and the second relative position.

4. A surgical portal apparatus as defined in claim 3, further including a switch positioned within the housing, the switch adapted to be engaged by the surgical object during introduction of the surgical object within the housing to activate the motor and thereby cause movement of the leaf members of the iris seal from the first relative position to the second relative position.

5. A surgical portal apparatus as defined in claim 4, wherein the switch is disposed proximal of the seal.

6. A surgical portal apparatus as defined in claim 5, including a delay circuitry associated with the switch, the delay circuitry providing a predetermined period of time prior to the leaf members moving to the second relative position to allow the surgical object to pass through the iris seal.

7. A surgical portal apparatus as defined in claim 4, wherein the switch is located distal to the iris seal.

8. A surgical portal apparatus as defined in claim 1, further including a manual switch mounted to the housing and operatively connected to the leaf members of the iris seal, the manual switch dimensioned for engagement by a clinician and manipulated to move the leaf members between the first and second relative positions.

9. A surgical portal apparatus as defined in claim 1 wherein the motor is adapted to deactivate when the resistive circuitry detects a threshold load on the motor to thereby releasably secure the leaf members in the second relative position.

10. A surgical portal apparatus comprising:
a housing;
a portal member extending from the housing, the portal member dimensioned for positioning within tissue, the housing and the portal member defining a longitudinal opening for permitting passage of a surgical object;
an iris seal disposed within the housing, the iris seal including a plurality of leaf members adapted for movement to control a dimension of a passage extending through the leaf members; and
an actuation mechanism associated with the leaf members, the actuation mechanism including a motor and a switch coupled with the motor, the switch being positioned and adapted to be engaged by the surgical object during introduction through the longitudinal opening, to thereby activate the motor and cause movement of the leaf members to control the dimension of the passage.

11. A surgical portal apparatus as defined in claim 10, wherein the leaf members are moveable from a first relative position defining a first dimension of the passage to a second relative position defining a second dimension of the passage less than the first dimension during introduction of the surgical object.

12. A surgical portal apparatus as defined in claim 11, wherein the leaf members are dimensioned and configured to establish a substantial sealing relationship with the surgical object when in the second relative position.

13. A surgical portal apparatus as defined in claim 11, further comprising a resistive circuitry associated with the motor and adapted to detect an increase of load on the motor and to thereby releasably secure the leaf members in the second relative position.

14. A surgical portal apparatus as defined in claim 11 wherein the switch is dimensioned and adapted to cooperate with the motor and permit the leaf members to assume the first relative position thereof upon removal of the surgical object.

15. A surgical portal apparatus as defined in claim 10, wherein the switch is disposed proximal of the seal.

16. A surgical portal apparatus as defined in claim 15, including a delay circuitry associated with the switch, the delay circuitry providing a predetermined period of time prior to the leaf members moving to the second relative position to allow the surgical object to pass through the iris seal.

17. A surgical portal apparatus as defined in claim 10, wherein the switch is located distal to the iris seal.

18. A surgical portal apparatus as defined in claim 10 wherein the leaf members are dimensioned and configured to define a substantially closed passage in the absence of the surgical object.

19. A surgical portal apparatus as defined in claim 10 wherein the switch is disposed within one of the housing or portal member.

20. A surgical portal apparatus comprising:
a housing;
a portal member extending from the housing, the portal member dimensioned for positioning within tissue, the portal member including a longitudinal opening for permitting passage of a surgical object;
an iris seal disposed within the housing and defining an opening therethrough and being adapted to establish a substantial sealing relationship with the surgical object introduced within the opening, the iris seal including a plurality of leaf members, the leaf members being pivotally mounted relative to the housing and adapted for pivotal movement from a first relative open position toward a second relative closed position; and
an actuation mechanism associated with the leaf members, the actuation mechanism including a motor, the motor effecting pivotal movement of the leaf members from the first relative position toward the second relative position.

21. A surgical portal apparatus as defined in independent claim 20 wherein the actuation mechanism includes a switch disposed within the housing or the portal member and coupled with the motor, the switch being positioned and adapted to be engaged by the surgical object during introduction thereof, to thereby activate the motor and cause movement of the leaf members from the first relative position toward the second relative position.

22. A surgical portal apparatus as defined in claim 20, further comprising a resistive circuitry associated with the motor and adapted to detect an increase of load on the motor and to thereby effect releasable securement of the leaf members in the second relative position.

* * * * *